US012133862B2

(12) United States Patent
Aiken et al.

(10) Patent No.: US 12,133,862 B2
(45) Date of Patent: *Nov. 5, 2024

(54) IMPLANTABLE PHARMACEUTICAL COMPOSITION PREPARED FROM COMPONENTS CONSISTING OF CALCIUM SULFATE ALPHA-HEMIHYDRATE, VANCOMYCIN AND GENTAMICIN

(71) Applicant: Biocomposites Limited, Staffordshire (GB)

(72) Inventors: Sean Sydney Aiken, Staffordshire (GB); Phillip Anthony Laycock, Staffordshire (GB); John Joseph Cooper, Staffordshire (GB); John Stephen Bratt, Staffordshire (GB); Michael Christopher James Harris, Staffordshire (GB)

(73) Assignee: BIOCOMPOSITES LIMITED, Staffordshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/842,689

(22) Filed: Jun. 16, 2022

(65) Prior Publication Data

US 2022/0401471 A1 Dec. 22, 2022

(30) Foreign Application Priority Data

Jun. 18, 2021 (GB) .................................... 2108727

(51) Int. Cl.
*A61K 33/06* (2006.01)
*A61K 9/16* (2006.01)
*A61K 31/7036* (2006.01)
*A61K 38/14* (2006.01)

(52) U.S. Cl.
CPC ............ *A61K 33/06* (2013.01); *A61K 9/1682* (2013.01); *A61K 31/7036* (2013.01); *A61K 38/14* (2013.01)

(58) Field of Classification Search
CPC .................................................... A61K 33/06
See application file for complete search history.

(56) References Cited

U.S. PATENT DOCUMENTS 6,780,391 B1 8/2004 Cooper
2013/0341820 A1 12/2013 Laycock et al.

FOREIGN PATENT DOCUMENTS

WO WO1996027346 A1 9/1996
WO WO1996/27346 * 12/1996

OTHER PUBLICATIONS

Deng-Xing et al. Effect of Particle Size Ratios on the Physical and Chemical Properties of Surgical-Grade Calcium Sulfate Hemihydrate. (Year: 2019).*
Aiken et al. Local Release of Antibiotics for Surgical Site Infection Management Using HighPurity Calcium Sulfate: An in Vitro Elution Study. (Year: 2015).*
GB Search Report, Application No. GB2108727.5, Date of Search Jul. 7, 2021, 2 pages.
World Neurosurgery, vol. 132, 2019, pp. E447-E454, Yang et al., Entitled: "Transforaminal Lumbar Interbody Fusion with Antibiotics Delivered by CaSO4 Drug Carrier System for Pyogenic Spondylodiscitis".
International Orthopaedics, vol. 43, 2019, pp. 1061-1070, Badie et al., Entitled: "One-stage surgery for adult chronic osteomyelitis: concomitant use of antibiotic-loaded calcium sulphate and bone marrow aspirate".
The Foot, vol. 27, 2016, pp. 36-40, Morley et al., Entitled: "Calcium sulphate as a drug delivery system in a deep diabetic foot infection".
Diabetes Care. vol. 38, 2015, pp. e79-e80, Jogia et al., Entitled: "Use of Highly Purified Synthetic Calcium Sulfate Impregnated With Antibiotics for the Management of Diabetic Foot Ulcers Complicated by Osteomyelitis", Available from https://care.diabetesjournals.org/content/38/5/e79.
Plastic and Reconstructive Surgery, vol. 141, No. 4, 2018, pp. 486e-492e, Kenna et al., Entitled: "Absorbable Antibiotic Beads Prophylaxis in Immediate Breast Reconstruction".
Advances in Skin and Wound Care, vol. 24, No. 11, 2011, pp. 515-523, Christopher Gauland, Entitled: "Managing Lower-Extremity Osteomyelitis Locally with Surgical Debridement and Synthetic Calcium Sulfate Antibiotic Tablets".
Intertek Chemicals and Pharmaceuticals, Apr. 2013, pp. 1-6, Zielinski et al., Entitled: "Physical Characterization: Surface Area and Porosity", http://www.intertek.com/chemicals.
Antimicrobial Agents and Chemotherapy, aac.asm.org, vol. 59, No. 1, 2015, pp. 111-120, Howlin et al., Entitled: "Antibiotic-Loaded Synthetic Calcium Sulfate Beads for Prevention of Bacterial Colonization and Biofilm Formation in Periprosthetic Infections", Available from https://www.ncbi.nlm.nih.gov/pmc/articles/PMC4291338/.
Biomedical Materials vol. 12, 2017, pp. 1-10, Howlin et al., Entitled: "Biofilm prevention of gram-negative bacterial pathogens involved in periprosthetic infection by antibiotic-loaded calcium sulfate beads in vitro".
GB Search Report, Application No. GB2108729.1, Date of Search Jul. 7, 2021, 2 Pages.
Journal of Biomaterials Applications, 2016, pp. 1-9, Cooper et al., Entitled: "Elution profiles of tobramycin and vancomycin from high-purity calcium sulphate beads incubated in a range of simulated body fluids".
Journal of Biomedical Materials Research Part B: Applied Biomaterials, 2013, vol. 00B, Issue 00, pp. 1-7, Roberts et al., Entitled: "Size and composition of synthetic calcium sulfate beads influence dissolution and elution rates in vitro", Available from: https://onlinelibrary.wiley.com/doi/abs/10.1002/jbm.b.33045.

(Continued)

*Primary Examiner* — Sarah Alawadi
(74) *Attorney, Agent, or Firm* — DAY PITNEY LLP; George N. Chaclas; Anthony A. Kassas (57) ABSTRACT

The present disclosure concerns a composition for an implantable pharmaceutical composition prepared from components consisting only of calcium sulfate α-hemihydrate in combination with two antibiotics, vancomycin and gentamicin, for the treatment of infection in bone and soft tissue.

17 Claims, 5 Drawing Sheets

(56) References Cited

OTHER PUBLICATIONS

Journal of Clinical Nephrology and Research, vol. 7, Issue 1: 2020, pp. 1-8, Maale et al., Entitled: "High Local Delivery Systems of Antibiotics in the Treatment of Biofilm Related Infections without Serum Toxic Levels", Available from https://www.jscimedcentral.com/Nephrology/nephrology-7-1098.pdf.

Journal of Orthopaedic Research, 2018, pp. 3081-3085, Moley et al., Entitled: "Reduction in Pseudomonas aeruginosa and *Staphylococcus aureus* biofilms from implant materials in a diffusion dominated environment", Available from https://onlinelibrary.wiley.com/doi/full/10.1002/jor.24074.

Journal of Shoulder and Elbow Surgery, Elsevier.com, vol. 26, 2017, pp. 553-563, Howlin et al., Entitled: "Prevention of Propionibacterium acnes biofilm formation in prosthetic infections in vitro".

EP Search Report in Application No. EP 22 17 6475, dated Nov. 1, 2022, 3 pages.

EP Search Report in Application No. EP 22 17 6404, dated Oct. 24, 2022, 4 pages.

Cooper, J.J., et al., "A new acoustic method to determine the setting time of calcium sulfate bone cement mixed with antibiotics", Biomedical Materials, Institute of Physics, vol. 9, No. 4, Jun. 30, 2014, p. 45006, XP020268531, 6 pages.

\* cited by examiner

FIG. 5

IMPLANTABLE PHARMACEUTICAL COMPOSITION PREPARED FROM COMPONENTS CONSISTING OF CALCIUM SULFATE ALPHA-HEMIHYDRATE, VANCOMYCIN AND GENTAMICIN

FIELD OF THE INVENTION

The present disclosure concerns a pharmaceutical composition for delivery of an implantable drug/drug device combination prepared from components consisting only of calcium sulfate α-hemihydrate in combination with two antibiotics, vancomycin and gentamicin, which are provided in the forms of vancomycin hydrochloride and gentamicin sulfate, for the treatment of infection in bone and soft tissue. Both sets of terms for the antibiotics will be used herein, and they are considered to be interchangeable with each other within the context of the present disclosure. The composition is typically prepared for implantation as absorbable beads into infected surgical sites in both bone and soft tissue. In addition, the disclosure relates to a method of formation of the aforementioned composition, which may be in the form of beads or pellets, and to the resultant physical properties of the composition when combined at a specific dose-weight combination.

BACKGROUND OF THE INVENTION

Studies of the use of calcium sulfate bone void fillers in conjunction with antibiotics for direct introduction into an infected surgical site have shown encouraging results. In addition to facilitating the regeneration of bone, they provide high local levels of antibiotics, thus also offering the beneficial effect of filling the dead space left by debridement.

Figure 1:
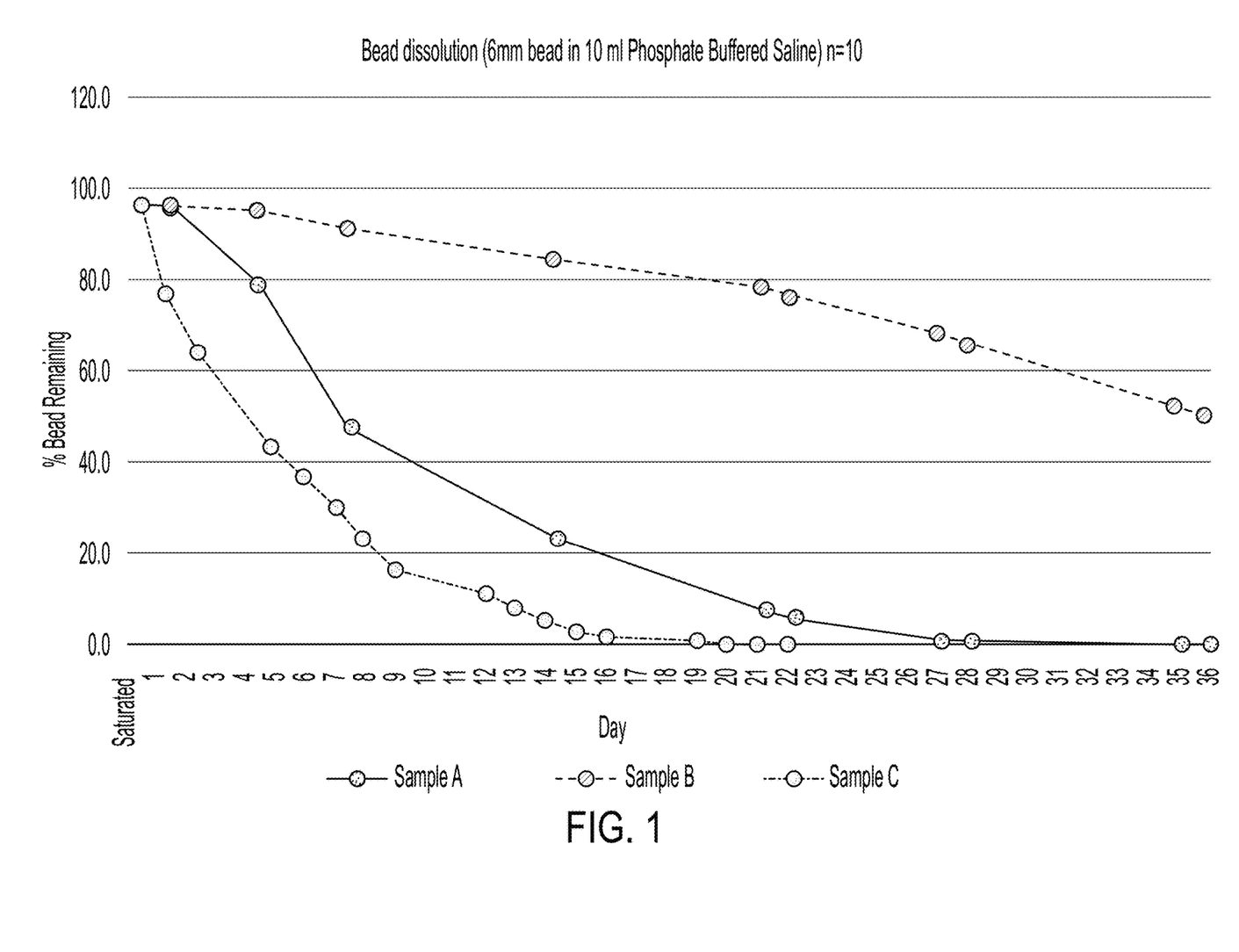
FIG. 1 illustrates the variation in dissolution between two commercially available calcium sulfates and the calcium sulfate α-hemihydrate of the disclosure, with different liquid/powder ratios as shown in Table 1 below, in accordance with the present disclosure.

The dissolution rate of calcium sulfate in the body can vary greatly as a result of differing manufacturing processes for the calcium sulfate. The addition of varying quantities of calcium sulfate dihydrate and/or potassium sulfate to the hemihydrate powder is often used to accelerate setting times of calcium sulfate beads or pellets; however, this can lead to differences in porosity and pore size which can make the dissolution rate variable to a significant degree. The graph depicted in FIG. 1 shows the variation in dissolution rates between two commercially available calcium sulfates and the calcium sulfate α-hemihydrate used in the present disclosure, each of which have different methods of manufacture.

A pharmaceutical grade of calcium sulfate material, suitable for use as a carrier of therapeutic agents to the body, has the levels of purity demanded by the pharmaceutical and medical device industries. It is often used as an excipient in tablet formulations. However, this high purity calcium sulfate material, which is generally produced by chemical precipitation reactions utilizing reagents having the necessary high levels of purity, and is presented in dihydrated form, has a fine particle size and high specific surface area. When treated by heat (either 'wet' or 'dry'), the calcium sulfate material produces an α-hemihydrate form of calcium sulfate having a high water demand.

The α-hemihydrate form is therefore required to be mixed with a relatively large quantities of water containing the therapeutic agents, as much as a liquid:powder ratio of 1:1 by weight, in order to form a paste consistency suitable for incorporation of therapeutical reagents for implantation. The powder in the liquid:powder ratio refers to the calcium sulfate material, while the liquid refers to the aqueous solution containing the therapeutic agents antibiotics. This gives a set, dihydrate form having a high porosity, low strength and low density and thus a rapid rate of dissolution within the body of a patient. This results in too rapid a release of the incorporated drug(s). This situation in certain patients and surgical procedures may result in adverse events such as hypercalaemia and acute kidney injury to the patient.

In addition, many commercially available forms of calcium sulfate α-hemihydrate contain additional excipients such as calcium sulfate dihydrate, potassium sulfate, trisodium phosphate and sodium phosphate to accelerate or slow down the setting time, or calcium stearate to slow down the absorption rate. Therefore, such materials cannot be considered to be a pure calcium sulfate.

SUMMARY OF THE INVENTION

In view of the foregoing, there is a significant need in the art for a pharmaceutical composition for delivery of an implantable drug/drug device combination prepared from components consisting only of calcium sulfate α-hemihydrate in combination with two antibiotics, vancomycin and gentamicin.

The present disclosure therefore provides a pharmaceutical composition prepared from components consisting only of:
  a) 18.4 g pharmaceutical grade, phase pure calcium sulfate α-hemihydrate;
  b) 500 mg of vancomycin hydrochloride; and
  c) 240 mg of gentamicin sulfate;
wherein the calcium sulfate α-hemihydrate is prepared by first converting a source of pharmaceutical grade calcium sulfate dihydrate to soluble calcium sulfate anhydrite by hydrothermal treatment in suspension, and then converting the resulting soluble anhydrous calcium sulfate to calcium sulfate α-hemihydrate by the following steps:
  i) adding the calcium sulfate dihydrate to a quantity of water in a water:calcium sulfate dihydrate ratio of 0.3:1-0.5:1 to form a suspension and autoclaving the suspension at 235-265° C. for 1-2 hours to dehydrate to form soluble calcium sulfate anhydrite;
  ii) allowing the soluble calcium sulfate anhydrite to cool in the autoclave in suspension to rehydrate back to calcium sulfate dihydrate; and
  iii) draining of excess water and autoclaving the rehydrated calcium sulfate dihydrate at 110-150° C. for 1-2 hours to convert the rehydrated calcium sulfate dihydrate to calcium sulfate α-hemihydrate.

Once the calcium sulfate α-hemihydrate has been formed in step (iii), the product is typically ground to a powder for further processing.

The water:calcium sulfate dihydrate ratio in step (i) may typically be in the range of 0.4:1-0.45-1, such as between about 0.42:-0.43:1.

The autoclaving in step (i) may typically be carried out at about 250° C. for about 90 minutes; while the autoclaving in step (iii) may typically be carried out at about 130° C. for about 90 minutes.

The vancomycin hydrochloride is typically added in the form of a powder and the gentamicin sulfate is typically added in the form of a liquid. Combining the liquid gentamicin sulfate with vancomycin hydrochloride powder forms a suspension containing vancomycin and gentamicin. The above-described method provides a low water demand (pharmaceutical grade) calcium sulfate α-hemihydrate. The liquid:powder ratio necessary then to form a 'paste' consistency suitable for incorporating the vancomycin hydrochloride and gentamicin sulfate into the calcium sulfate α-hemihydrate would ideally be in the range 0.26-0.35:1, more typically 0.28-0.32:1 parts by weight, i.e. the solution required to hydrate the calcium sulfate α-hemihydrate when forming beads containing the vancomycin hydrochloride and gentamicin sulfate. The powder in the liquid:powder ratio herein refers to the calcium sulfate α-hemihydrate, while the liquid refers to the suspension containing vancomycin and gentamicin antibiotics. By way of comparison, an alternative calcium sulfate which is commercially available has a higher water demand of 0.39:1, which results in a higher porosity, lower strength and lower density and thus a more rapid rate of dissolution within the body of a patient. This is undesirable.

The calcium sulfate α-hemihydrate requires a water demand (or solution) in the defined range to fully convert to dihydrate, i.e. set hard. As used herein, the "solution" is liquid gentamicin combined with vancomycin, which forms a suspension containing vancomycin and gentamicin. If the amount of solution required is too high, then the porosity is increased and therefore the dissolution rate will be too high. Too low a water demand will compromise strength.

Vancomycin is a tricyclic glycopeptide antibiotic, which inhibits the synthesis of bacterial cell wall membranes in susceptible bacteria. Its spectrum is limited to the treatment of infections caused by aerobic and anaerobic gram-positive bacteria, including *Staphylococcus aureus* and *Staphylococcus epidermidis* (including methicillin-resistant strains) and *Streptococcus* Species. Vancomycin is not effective on gram negative strains because the outer membrane of this group of bacteria contains a peptidoglycan polymer layer impermeable to the drug.

Gentamicin is a broad-spectrum aminoglycoside antibiotic. Its mode of action is by binding to 30S subunit bacterial ribosomes. This impairs the proofreading of t-RNA resulting in the production of faulty proteins that insert into the cytoplastic membrane, killing the bacteria. Although indicated for gram-negative bacteria, including *Citrobacter* Species, *Enterobacter* Species, *Escherichia coli*, *Klebsiella* Species, *Proteus* Species, *Serratia* Species and *Pseudomonas aeruginosa* and gram-positive *Staphylococcus* Species, gentamicin has limited effectiveness against streptococci and anaerobic bacteria. Gentamicin has a long history of local clinical application by being combined in polymethylmethacrylate (PMMA) bone cement due to its stability at high temperatures during the hardening phase.

For some serious infections, the efficacy of vancomycin is not always satisfactory. The rise of vancomycin resistant strains is also concerning. The combination of vancomycin with gentamicin has shown promising results in-vitro and has also been demonstrated clinically.

Porosity is an important characteristic of a drug eluting material. There is a direct correlation between pore size and dissolution rate. The more porous the material, the more fluids can penetrate the material, accelerating the rate of dissolution and therefore allowing the contained medicaments to be released. The porosity of the material is determined by the purity of the calcium sulfate α-hemihydrate, the speed of crystallization to dihydrate (i.e. the setting time) and the dose of the active pharmaceutical ingredients. In addition, the volume of aqueous solution containing the active pharmaceutical ingredients—i.e. the vancomycin and gentamicin—is critical to the final composition of the set beads or pellets. Adding too little of the aqueous solution results in only a partial conversion to calcium sulfate dihydrate, producing a weaker, more soluble biphasic material. Conversely, too much liquid results in surplus water for crystallization, which will not take part in the reaction and remains as free water in the material, contributing to the subsequent porosity and will eventually evaporate leaving a weaker material. The liquid to powder ratio is therefore an important parameter to produce a finished material with the ideal surface area and pore size, critical factors in the dissolution of the beads and consequently the elution of the added medicaments.

Porosity and surface area of a material can be measured by the Brauner, Emmett and Teller (BET) technique or alternatively by mercury intrusion porosimetry. The BET technique involving nitrogen adsorption is widely used for detecting open pores mainly in the micro ($\leq 2$ nm) to mesopore (2-50 nm) region. The volume of nitrogen adsorbed to the surface of the material is measured at the boiling point of nitrogen (−196° C.). At this temperature, the nitrogen gas is below the critical temperature and so condenses on the surface in a monolayer. As the size of the nitrogen atom/molecule is known, the amount of adsorbed (condensed) gas is correlated to the total surface area of the particles including pores at the surface.

Average pore size distribution can be deduced according to the Barrett-Joyner-Halenda (BJH) method. Where BET theory measures the specific surface area of materials, BJH theory is a pore size distribution determination method. This method determines pore area and specific pore volume using adsorption and desorption techniques and characterizes pore size distribution independent of external area due to particle size of the sample.

Setting time of the material can be determined by a variety of methods. The surface penetration test involves applying a weighted Vicat or Gilmore needle to the surface of the material. The material is deemed to be set when it has either penetrated to a given depth (Vicat) or developed sufficient strength to support the needle and it no longer makes an indentation (Gilmore). Both the Vicat and Gilmore tests are the subject of multiple standards, including ASTM. An alternative method is acoustic monitoring, where the sound frequencies produced when dropping the material onto a hard surface from a set height are recorded. Set time is confirmed when the frequencies match those of a control sample that is fully set. A more accurate method for determining set time is by monitoring the temperature of the setting mass with a calibrated thermocouple inserted into the material. The calcium sulfate crystallization reaction is exothermic, and the mass will continue to increase in temperature until the reaction has completed, at which point the material will start to reduce in temperature. The peak of the temperature curve indicates the final set time.

The present disclosure seeks to provide an implantable composition for treatment of localized infections in the body by providing a dual antibiotic loaded material produced from materials consisting only of a pharmaceutically pure calcium sulfate α-hemihydrate, in combination with two antibiotics, vancomycin and gentamicin, in particular amounts, together providing a synergistic effect.

The present disclosure provides a composition that not only provides a local delivery carrier for the two antibiotics, but has specific properties necessary to provide a controlled reproducible dissolution rate. Pore size, surface area and compressive strength all determine the physical properties of the set beads in respect to the dissolution rate and elution kinetics of the two antibiotics. The purity of the calcium sulfate free of setting aids and other processing excipients in combination with a fixed dose of two antibiotics, which together target a wider range of bacterial infections is described.

It should be appreciated that the subject technology can be implemented and utilized in numerous ways, including, without limitation, as a process, an apparatus, a system, a device, a method for applications now known and later developed. These and other unique features of the composition disclosed herein will become more readily apparent from the following description and the accompanying drawings.

TABLE 1

Three calcium sulfates manufactured with different liquid/powder ratios

|  | Liquid/Powder Ratio |
| --- | --- |
| Sample 1 (Synthecure ®) | 0.240:1 |
| Sample 2 (the calcium sulfate α-hemihydrate of the disclosure) | 0.320:1 |
| Sample 3 (InterSep ®) | 0.395:1 |

DETAILED DESCRIPTION

The advantages, and other features of the method disclosed herein, will become more readily apparent to those having ordinary skill in the art from the following detailed description of certain preferred embodiments taken in conjunction with the drawings, which set forth representative embodiments of the present invention and wherein like reference numerals identify similar structural elements. It is understood that references to the figures such as up, down, upward, downward, left, and right are with respect to the figures and not meant in a limiting sense.

The present disclosure provides a pharmaceutical composition prepared from components consisting of 18.4 g pharmaceutical grade, phase pure calcium sulfate α-hemihydrate, 500 mg of vancomycin hydrochloride; and 240 mg of gentamicin sulfate; where the calcium sulfate α-hemihydrate is prepared using the steps (i)-(iii) discussed above. The composition is typically provided in the form of beads or pellets 2, which are formed by setting amounts of a paste of the composition within a mold mat 4 having two sides, and containing cavities 6 of a specific size and shape to produce cylindrical beads 2 with one hemispherical end for implantation into a surgical site on either side of mold mat 4.

The calcium sulfate used to prepare the composition is calcium sulfate α-hemihydrate. The calcium sulfate α-hemihydrate is of a high purity exceeding the ASTM standard for calcium sulfate. The composition of the disclosure is prepared using only calcium sulfate α-hemihydrate, vancomycin hydrochloride and gentamicin sulfate, and is free of any processing and setting aids, including calcium sulfate dihydrate, potassium phosphate, sodium chloride, sodium sulfate or calcium stearate. This simplifies the process, makes it less expensive, and also reduces the variability in porosity and pore size of the composition.

Figure 2:
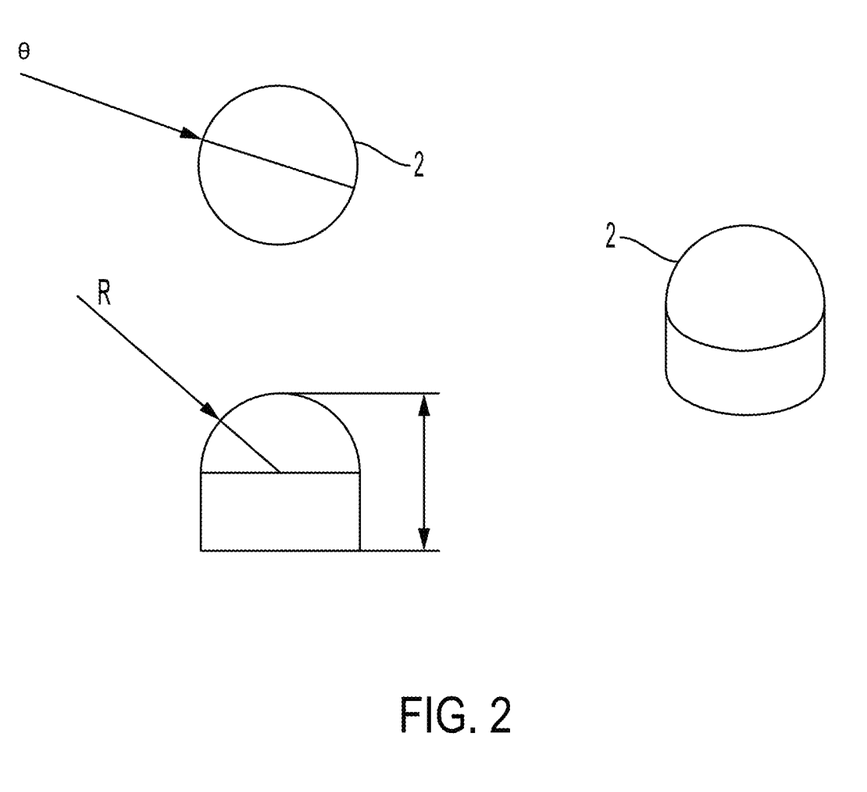
FIG. 2 illustrates a plan view, sectional side view, and perspective view of a 3 mm bead having a diameter of 3 mm at its widest point, and made of the composition described in the present disclosure.

The vancomycin is provided in the form of its hydrochloride salt. The vancomycin hydrochloride will typically be in powder form. The gentamicin is provided in the form of its sulfate salt. The gentamicin sulfate will typically be in the form of a solution and is used for both solubilizing and suspending the vancomycin hydrochloride powder and hydrating the calcium sulfate α-hemihydrate to form the composition, which is typically in the form of set beads or pellets 2.

Figure 3:
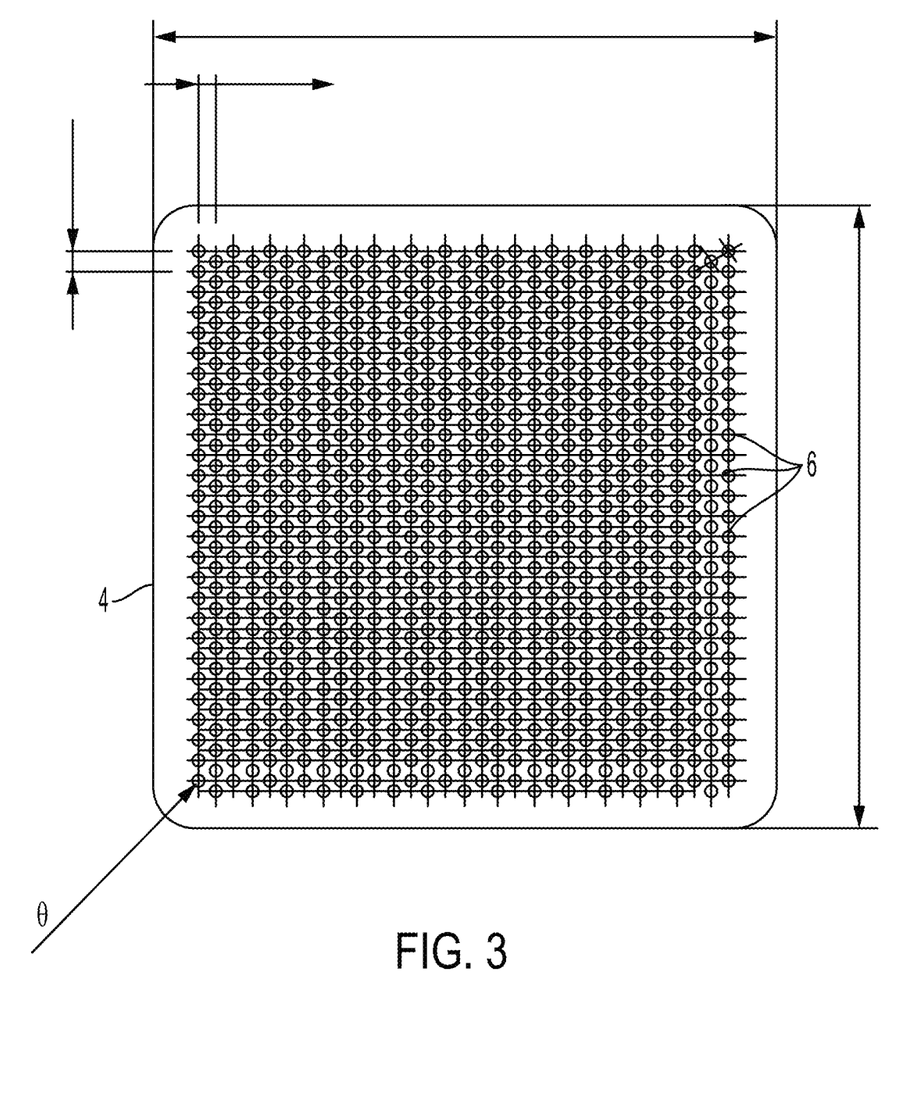
FIG. 3 illustrates a plan view of a mold used to make the beads in FIG. 2, having a plurality of cavities thereon, the diameter of which is 3 mm.

If the composition is in the form of beads or pellets 2, they are formed by measuring the gentamicin sulfate solution at the appropriate dose and adding the solution to the specified weight of vancomycin powder. The vancomycin partly dissolves in the gentamicin solution to produce a suspension containing the two antibiotics. The suspension is then applied to the specified weight of calcium sulfate α-hemihydrate powder and mixed, typically for about 20 seconds. The resultant paste is then applied to a bead mold 4 and allowed to set.

Once set, the resultant beads 2 are then removed from the mold 4 and are ready for implantation into the surgical site. The beads 2 possess a specific surface area and pore size distribution allowing for a predictable and controlled rate of dissolution and drug elution when measured in vitro. In one specific embodiment, the beads 2 are cylindrical, having a diameter between 2.8 mm and 3.2 mm at their widest point. One end of the bead 2 is hemispherical. The bead mold 4 will typically contain a total of 837 cavities 6 to incorporate all the paste.

Figure 4:
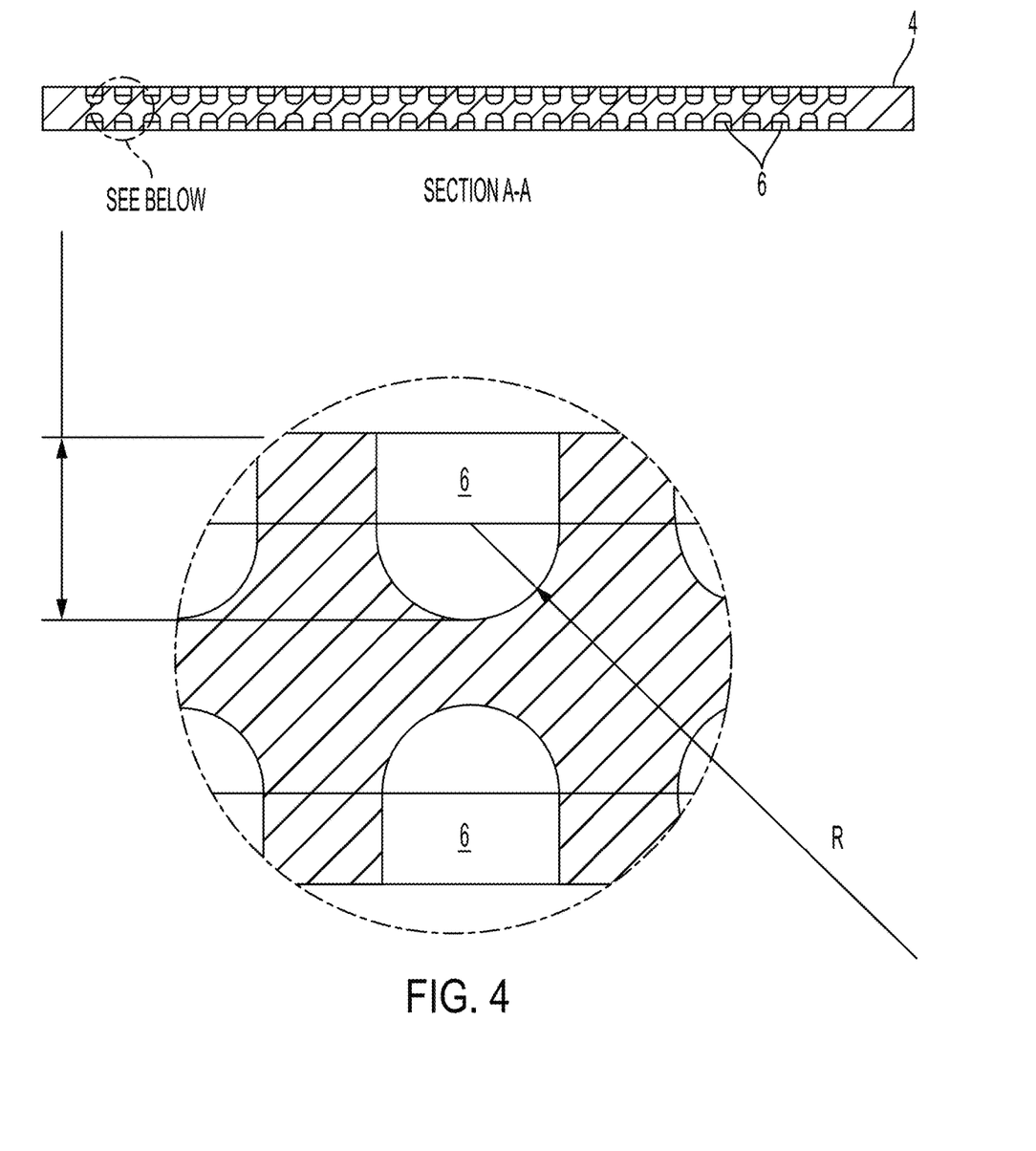
FIG. 4 illustrates two sectional side views of a bead mold, a first section side view with a wider perspective two-sided mold with bead cavities on either side.
Figure 5:
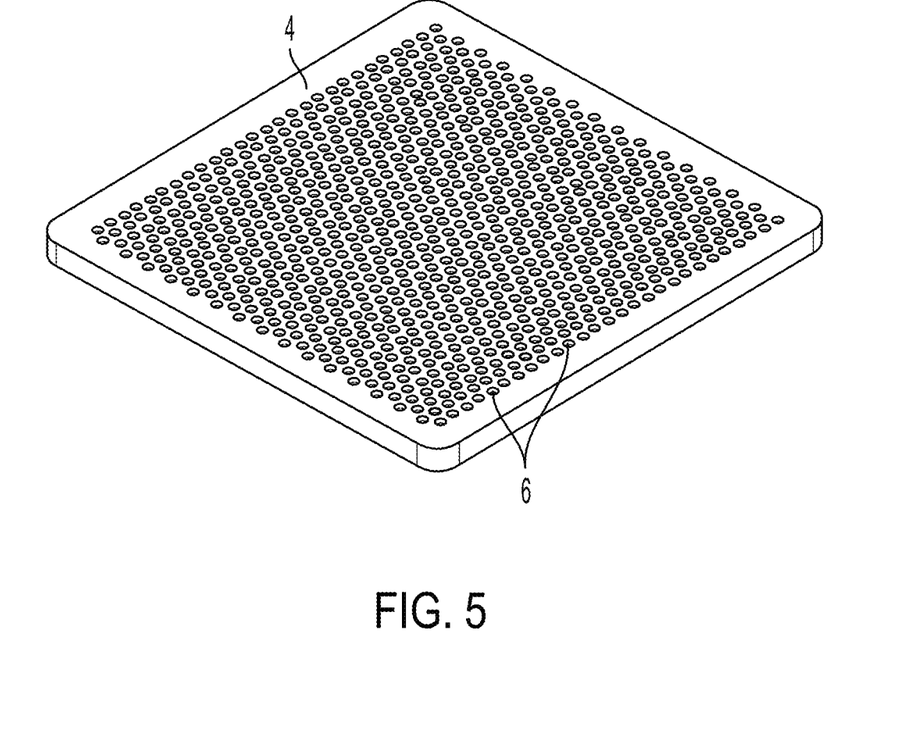
FIG. 5 illustrates and additional another perspective view of the bead mold according to FIG. 3, further illustrating the plurality of cavities thereon.

The bead mold 4 is typically a two-sided mold with bead cavities 6 on both sides. This facilitates easier removal of the beads by adding flexibility to the mold. The cavities 6 are typically identical on both sides. In one specific embodiment, the bead mold 4 is square in shape having sides of 152.5 mm and a depth of 7.5 mm.

The physical properties of the beads 2 are a product of the antibiotic doses and the weight of the calcium sulfate hemihydrate powder used to make them. The ratio of drug concentration to hemihydrate powder (i.e. the liquid:powder ratio referenced above) is critical to the performance of the beads 2 once implanted. The liquid:powder ratio is linked to bead set time, compressive strength and elution profile of both pharmaceutical ingredients.

As discussed above, the porosity of the composition is determined in part by the volume of aqueous solution containing the active pharmaceutical ingredients. Adding too little of the aqueous solution to the powder results in only a partial conversion to calcium sulfate dihydrate, producing a weaker, more soluble biphasic material. Conversely, too much liquid results in surplus water for crystallization, which will not take part in the reaction and remains as free water in the material, contributing to the subsequent porosity and leaving a weaker material. The liquid to powder ratio is an important parameter to produce a finished material with the ideal surface area and pore size, critical factors in the dissolution of the beads and consequently the elution of the added pharmaceutical ingredients.

The ideal liquid to powder ratio to fully convert the calcium sulfate α-hemihydrate is in the range of 0.26-0.35:1, more typically 0.28-0.32:1. The liquid to powder ratio of other commercially available calcium sulfate products use ratios, which are either lower or higher than this, as shown in Table 1 above, due to them being manufactured in different ways to the calcium sulfate α-hemihydrate used in the present disclosure.

In one specific embodiment, the dose of gentamicin sulfate in solution is 40 mg/ml. 6 ml of the gentamicin sulfate in solution is used to partially dissolve the vancomycin hydrochloride at a dose of 500 mg and the resultant aqueous suspension contains 83.33 mg/ml of vancomycin hydrochloride. This will fully hydrate 18.4 g of calcium sulfate α-hemihydrate powder.

In the specific embodiment of 18.4 g calcium sulfate alpha hemihydrate with 500 g vancomycin and 240 mg gentamicin prepared as described, the set beads 2 typically have specific properties in terms of BET surface area of between about 0.2 $m^2/g$ and 0.8 $m^2/g$; more typically between about 0.4 $m^2/g$ and 0.6 $m^2/g$.

According to one embodiment of the disclosure, the beads or pellets 2 have a BJH adsorption average pore diameter (4 v/A) area deduced according to the Barrett-Joyner-Halenda (BJ11) pore size distribution method between about 10 nm and 25 nm.

The beads 2 when produced according to the aforementioned embodiments, have a setting time of under 20 minutes as defined as the time required from the combination of the aqueous suspension to the calcium sulfate alpha-hemihydrate until hardening is achieved. The disclosed embodiments produce antibiotic loaded calcium sulfate dihydrate beads 2 that maintain sufficient compressive strength that is not compromised by the addition of antibiotics. According to one embodiment, the compressive strength is between 10 and 20 MPa at 1 hour after mixing.

The beads 2 produced using the aforementioned method may be used in surgical procedures as part of an infection management strategy where they absorb and elution the full amount of vancomycin and gentamicin at the surgical site reducing the risk of systemic toxicity compared to systemic administration of the two antibiotics.

Also provided by the present disclosure is a method of administering two antibiotics to a patient, the method comprising inserting a composition as defined hereinabove into a surgical void in a patient.

Also provided by the present disclosure is a method of treating infection in bone and soft tissue, the method comprising administering a composition as defined hereinabove into a surgical void in a patient.

EXAMPLES

Example 1

Demonstrate Synergistic Effect of VG Over G Against Gram Positive Staph Strains 18.4 g of calcium sulfate α-hemihydrate was combined with either 240 mg (6 ml) of gentamicin sulfate liquid or 240 mg (6 ml) of gentamicin sulfate liquid with 500 mg of vancomycin hydrochloride powder and formed into 6 mm beads 2 and allowed to set. Agar plates were seeded with 0.2 ml of an actively growing suspension of the relevant organism. The plates were transferred to an incubator for 30 minutes. The plates were then removed from the incubator and the beads 2 samples were placed on the surface. The plates were then re-incubated. On removal from the incubator, the plates were examined for the absence of growth as seen by a clear zone around the bead. Any zones of inhibition (ZOI) were measured and photographed. Zone sizes are shown in Tables 24 below.

TABLE 2

ZOI: *Staphyloccocus aureus* ATCC 6538

| Test Sample (6 mm bead) | Zone (mm) | | |
|---|---|---|---|
| | Sample 1 | Sample 2 | Sample 3 |
| CS + Gentamicin | 15-16 | 15-16 | 17-18 |
| CS + Vancomycin + Gentamicin | 20-21 | 20-21 | 20-21 |

TABLE 3

ZOI: *Staphyloccocus epidermidis* ATCC 12228

| Test Sample (6 mm bead) | Zone (mm) | | |
|---|---|---|---|
| | Sample 1 | Sample 2 | Sample 3 |
| CS + Gentamicin | 25-26 | 23-24 | 23-24 |
| CS + Vancomycin + Gentamicin | 25-26 | 26-27 | 26-27 |

TABLE 4

ZOI: MRSA NCTC 12493

| Test Sample (6 mm bead) | Zone (mm) | | |
|---|---|---|---|
| | Sample 1 | Sample 2 | Sample 3 |
| CS + Gentamicin | 16-17 | 14-15 | 16-17 |
| CS + Vancomycin + Gentamicin | 21-22 | 21-22 | 20-21 |

Example 2

Demonstrate Surface Area 18.4 g of calcium sulfate α-hemihydrate was combined with 240 mg (6 ml) of gentamicin sulfate liquid with 500 mg of vancomycin hydrochloride powder and formed into 3 mm beads 2 and allowed to set. A sample set of 3 beads 2 were selected at random for analysis. The beads 2 were vacuum degassed at room temperature and then isotherms were obtained using a nitrogen adsorption instrument (Tristar II Plus. Micromeritics Ltd.) Results are shown in Table 5 below.

TABLE 5

BET surface area of three lots of calcium sulfate combined with vancomycin and gentamicin

| Sample | BET Surface Area (m2/g) |
|---|---|
| Lot 1 Sample 1 | 0.346 |
| Lot 1 Sample 2 | 0.352 |
| Lot 1 Sample 3 | 0.372 |
| Lot 2 Sample 1 | 0.353 |
| Lot 2 Sample 2 | 0.355 |
| Lot 2 Sample 3 | 0.361 |

TABLE 5-continued

BET surface area of three lots of calcium sulfate combined with vancomycin and gentamicin

| Sample | BET Surface Area (m2/g) |
|---|---|
| Lot 3 Sample 1 | 0.292 |
| Lot 3 Sample 2 | 0.289 |
| Lot 3 Sample 3 | 0.294 |

Example 3

Demonstrate BJH Pore Size Distribution 18.4 g of calcium sulfate hemihydrate was combined with 240 mg (6 ml) of gentamicin liquid with 500 mg of vancomycin powder and formed into 3 mm beads 2 and allowed to set. A sample set of 3 beads 2 were selected at random for analysis. The beads 2 were vacuum degassed at room temperature and then isotherms were obtained using a nitrogen adsorption instrument (Tristar II Plus, Micromeritics Ltd.) Results are shown in Table 6.

TABLE 6

BJH Adsorption Average Pore Diameter of three lots of calcium sulfate combined with vancomycin and gentamicin

| Sample | BJH Adsorption Average Pore Diameter (4V/A) (nm) |
|---|---|
| Lot 1 Sample 1 | 13.6327 |
| Lot 1 Sample 2 | 13.8784 |
| Lot 1 Sample 3 | 13.4841 |
| Lot 2 Sample 1 | 19.4566 |
| Lot 2 Sample 2 | 19.1605 |
| Lot 2 Sample 3 | 17.5870 |
| Lot 3 Sample 1 | 18.0439 |
| Lot 3 Sample 2 | 19.1441 |
| Lot 3 Sample 3 | 17.1265 |

Example 4

Demonstrate Compressive Strength 18.4 g of calcium sulfate hemihydrate was combined with 240 mg (6 ml) of gentamicin liquid with 500 mg of vancomycin powder and applied to a mold mat to form cylinders of approximately 7 mm in diameter and 10 mm in height. The samples were then individually placed between compression plates on a single-column materials testing machine (Zwickiline, Zwick Roell) with a maximum deformation of 2 mm and upper force limit of 2000N and compressed at 0.5 mm/minute. Fmax was recorded (N) and converted to MPa. The compressive strength was recorded as 14.56 MPa (n=5) compared to unloaded calcium sulfate cylinders with a compressive strength of 18.3 MPa (n=5).

While the subject technology has been described with respect to preferred embodiments, those skilled in the art will readily appreciate that various changes and/or modifications can be made to the subject technology without departing from the spirit or scope of the subject disclosure. The appended claims are exemplary and may be combined and arranged in any manner including with multiple dependencies and the like. It is of course to be understood that the present disclosure is not intended to be restricted to the foregoing examples, which are described by way of example only.

We claim:

1. A pharmaceutical composition prepared from components consisting of:
   a) 18.4 g pharmaceutical grade, phase pure calcium sulfate α-hemihydrate;
   b) 500 mg of vancomycin hydrochloride; and
   c) 240 mg of gentamicin sulfate, the gentamicin sulfate in the form of a solution;
   wherein the calcium sulfate α-hemihydrate is prepared by first converting a source of pharmaceutical grade calcium sulfate dihydrate to soluble calcium sulfate anhydrite by hydrothermal treatment in suspension, and then converting the resulting soluble anhydrous calcium sulfate to calcium sulfate α-hemihydrate by:
   i) adding the calcium sulfate dihydrate to a quantity of water in a water:calcium sulfate dihydrate ratio of 0.3:1-0.5:1 to form a suspension and autoclaving the suspension at 235-265° C. for 1-2 hours to dehydrate to form soluble anhydrite;
   ii) allowing the soluble anhydrite to cool in the autoclave in suspension to rehydrate back to calcium sulfate dihydrate; and
   iii) draining off excess water and autoclaving again at 110-150° C. for 1-2 hours to convert the rehydrated calcium sulfate dihydrate to calcium sulfate α-hemihydrate.

2. The composition according to claim 1, wherein the vancomycin hydrochloride, is in a powder form, and wherein the vancomycin hydrochloride in a powder form and the gentamicin sulfate are combined together to form a suspension, and the suspension is combined with the calcium sulfate a-hemihydrate in powder form in a liquid:powder ratio of between 0.26 and 0.35 parts by weight.

3. The composition according to claim 2, wherein the liquid:powder ratio is between 0.28 and 0.32 parts by weight.

4. The composition according to claim 1, wherein the composition is in the form of beads or pellets, wherein the beads or pellets are optionally between about 2.8 and 3.2 mm in diameter at their widest point.

5. The composition according to claim 4, wherein the beads or pellets have a compressive strength of between 10 MPa and 20 MPa at 1 hour after setting.

6. The composition according to claim 4, wherein the beads or pellets have a BET specific surface area obtained using the Brunauer Emmett-Teller (BET) Method of between about 0.2 m2/g and 0.8 m2/g.

7. The composition according to claim 4, wherein the beads or pellets have a BJH adsorption average pore diameter calculated using the formula 4v/A area, according to the Barrett-Joyner-Halenda (BJH) pore size distribution method, of between 10 nm and 25 nm.

8. A method of manufacturing a composition for delivery of an implantable drug comprising:
   a) mixing 500 mg of vancomycin hydrochloride with 240 mg of gentamicin sulfate, the gentamicin sulfate being in the form of an aqueous solution, the gentamicin sulfate being in the form of a liquid, to produce a suspension containing vancomycin and gentamicin;
   b) combining said suspension with a powder consisting of 18.4 g of pharmaceutical grade, phase pure calcium sulfate a-hemihydrate to form a mixture;
   c) forming said mixture into beads or pellets;
   d) allowing the beads or pellets to set and solidify using a plurality of molds; and
   e) producing beads or pellets of the composition,
   wherein the calcium sulfate a-hemihydrate is prepared by first converting a source of pharmaceutical grade calcium sulfate dihydrate to soluble calcium sulfate anhydrite by hydrothermal treatment in suspension, and then converting the resulting soluble anhydrous calcium sulfate to calcium sulfate a-hemihydrate by:

i) adding the calcium sulfate dihydrate to a quantity of water in a water:calcium sulfate dihydrate ratio of 0.3:1-0.5:1 to form a suspension and autoclaving the suspension at 235-265° C. for 1-2 hours to dehydrate to form soluble anhydrite;

ii) allowing the soluble anhydrite to cool in the autoclave in suspension to rehydrate back to calcium sulfate dihydrate; and iii) draining off excess water and autoclaving again at 110-150° C. for 1-2 hours to convert the rehydrated calcium sulfate dihydrate to calcium sulfate a-hemihydrate.

9. The method according to claim 8, wherein:
a) the vancomycin hydrochloride is provided in the form of a powder, and
b) the beads or pellets of the composition are individually shaped as a cylinder with a single hemispherical end.

10. The method according to claim 8, wherein in step (b), the suspension containing the vancomycin hydrochloride and gentamicin sulfate is combined with the calcium sulfate α-hemihydrate in powder form in a liquid:powder ratio of between 0.26 and 0.35 parts by weight.

11. The method according to claim 10, wherein the liquid:powder ratio is between 0.28 and 0.32 parts by weight.

12. The method according to claim 8, wherein the volume of the aqueous solution to receive the vancomycin for a single dose of the composition is between about 5.5 ml and 7.5 ml.

13. The method according to claim 8, wherein the beads or pellets are prepared using a mold mat containing cavities wherein the size, spacing and geometric arrangement of cavities is such that any straight line drawn along the full length of the mold mat parallel to an edge of the mold mat in at least one direction and within the arrangement of cavities on the mat will always intersect at least one cavity.

14. The method according to claim 13, wherein the mold mat contains cavities on both sides of the mat.

15. The method according to claim 8, wherein the beads or pellets set in a time of between about 10 and 20 minutes as measured by the temperature rise method.

16. The method according to claim 15, wherein the setting time is determined by the insertion of a thermometer probe inside the mixture of beads or pellets to track changes in temperature over time.

17. A method of treating infection in bone and soft tissue, the method comprising administering the pharmaceutical composition according to claim 1 into a surgical void in a patient.

* * * * *